(12) United States Patent
Osypka

(10) Patent No.: US 7,128,600 B2
(45) Date of Patent: Oct. 31, 2006

(54) ADAPTER FOR ELECTRICAL STIMULATION LEADS

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 750 days.

(21) Appl. No.: 10/174,244

(22) Filed: Jun. 18, 2002

(65) Prior Publication Data
US 2003/0077943 A1    Apr. 24, 2003

Related U.S. Application Data

(60) Provisional application No. 60/378,423, filed on May 7, 2002, provisional application No. 60/338,227, filed on Dec. 6, 2001, provisional application No. 60/337,437, filed on Oct. 22, 2001.

(51) Int. Cl.
H01R 11/00 (2006.01)
(52) U.S. Cl. ...................... 439/502; 439/909
(58) Field of Classification Search .............. 439/502, 439/218, 909; 607/116, 115, 122, 123
See application file for complete search history.

(56) References Cited

U.S. PATENT DOCUMENTS

| | | | | |
|---|---|---|---|---|
| 4,214,804 A * | 7/1980 | Little | ................ | 439/502 |
| 4,452,248 A | 6/1984 | Keller, Jr. | | |
| 4,479,500 A | 10/1984 | Smits | | |
| 4,545,381 A | 10/1985 | Bournay, Jr. et al. | | |
| 4,628,934 A | 12/1986 | Pohndorf et al. | | |
| 5,000,177 A | 3/1991 | Hoffmann et al. | | |
| 5,007,864 A | 4/1991 | Stutz, Jr. | | |
| 5,026,371 A * | 6/1991 | Rydell et al. | ................ | 606/47 |
| 5,314,452 A | 5/1994 | Hirschberg et al. | | |
| 5,358,519 A | 10/1994 | Grandjean | | |
| 5,439,391 A | 8/1995 | McEtchin et al. | | |
| 5,470,346 A | 11/1995 | Adams | | |
| 5,662,692 A | 9/1997 | Paspa et al. | | |
| 5,676,694 A | 10/1997 | Boser et al. | | |
| 5,679,026 A | 10/1997 | Fain et al. | | |
| 5,911,719 A * | 6/1999 | Eggers | ................ | 606/31 |
| 5,937,950 A * | 8/1999 | Adams et al. | ............. | 174/72 R |
| 5,948,014 A | 9/1999 | Valikai | | |
| 6,006,135 A | 12/1999 | Kast et al. | | |
| 6,038,463 A | 3/2000 | Laske et al. | | |
| 6,078,839 A | 6/2000 | Carson | | |
| 6,190,385 B1 * | 2/2001 | Tom et al. | ................ | 606/48 |

(Continued)

FOREIGN PATENT DOCUMENTS

EP    0 428 279 A2    5/1991

(Continued)

OTHER PUBLICATIONS

Guidant catalog, pp. 237-240 (undated).

(Continued)

Primary Examiner—Hien Vu
(74) Attorney, Agent, or Firm—Scott D. Wofsy; Edwards Angell Palmer & Dodge LLP

(57) ABSTRACT

A lead adapter is disclosed which includes a connector portion having a connector configured for reception by an electrical stimulation device and a receptacle portion electrically connected to the connector portion and having at least two receptacles for operatively accepting lead connectors, wherein at least one of the receptacles of the receptacle portion is configured to operatively accept a different type of lead connector than another receptacle of the receptacle portion.

10 Claims, 4 Drawing Sheets

U.S. PATENT DOCUMENTS

2004/0014355 A1* 1/2004 Osypka et al. .............. 439/502
2005/0106940 A1* 5/2005 Murphy et al. ............. 439/610

FOREIGN PATENT DOCUMENTS

| EP | 0 599 567 A3 | 8/1996 |
| EP | 0 911 062 A1 | 4/1999 |
| WO | WO 99/30772 | 6/1999 |

OTHER PUBLICATIONS

European Patent Office Action dated Jun. 12, 2006.

* cited by examiner

ADAPTER FOR ELECTRICAL STIMULATION LEADS

CROSS-REFERENCE TO RELATED APPLICATIONS

The subject application claims the benefit of priority from U.S. Provisional Patent Application Ser. No. 60/337,437 filed Oct. 22, 2001, U.S. Provisional Patent Application Ser. No. 60/338,227 filed Dec. 6, 2001, and U.S. Provisional Patent Application Ser. No. 60/378,423 filed May 7, 2002 the disclosures of which are herein incorporated by reference in their entireties.

BACKGROUND OF THE INVENTION

1. Field of the Invention

The subject invention is directed generally to adapters for electrical stimulation leads, and more particularly, to adapters for connecting cardiac leads to electrical therapeutic and/or diagnostic devices such as cardiac pacemakers and/or defibrillators.

2. Background of the Related Art

Electrical stimulation devices for cardiac and neurological stimulation are well known in the medical filed. Cardiac stimulation devices are used for therapeutic and/or diagnostic purposes. These devices, which include cardiac pacemakers and implantable cardiac defibrillators, generally interface with cardiac tissue by means of implantable or otherwise attachable cardiac leads. These leads employ connector portions to operatively connect with matching receptacles located in the therapeutic and/or diagnostic devices.

In operation, electrical therapeutic and/or diagnostic devices for the heart send and/or receive electrical signals from heart tissue. These signals are carried to and from the devices through conductors which form part of the cardiac leads. In order to properly conduct the signals, the cardiac leads must make proper electrical contact with the electrical therapeutic and/or diagnostic devices.

Connectors typically include one or more electrical contact points or poles, to communicate signals between the electrical therapeutic and/or diagnostic device and the leads to which it is connected. These poles are either anodic or cathodic. Anodic poles are generally relatively positive in polarity and cathodic poles are generally relatively negative in polarity.

Connectors are available in various configurations which are often of standardized types readily recognized by those practicing in the art. Connector types may differ from one another in connector diameter, connector length, connector shape, placement of electrical contact points and other geometric or functional properties. It is well understood by those practicing in the art that connectors of one type cannot directly connect to receptacles designed to operatively accept a different type of connector. Receptacle type is thus determined by the connector type which the receptacle may operatively accept.

Common connector types well known in the art currently include: IS-I type (International Standard ISO 5841.3:1992) pacing/sensing connectors which have a 3.2 mm diameter and are available in unipolar or bipolar configurations; LV-1 type pacing/sensing connectors which have a 1.8 mm diameter and are available in unipolar and bipolar configurations (Guidant Corporation); and DF-1 type (International Standard ISO 11318:1993) defibrillator connectors which have a unipolar configuration.

Some leads, such as those used in conjunction with implantable cardiac defibrillator (ICD leads), employ multiple connectors. For example, leads are known which employ one or two DF-1 type connectors and one or two IS-1 type connectors, all of which are combined at a yoke portion of the lead.

It is envisioned that other standardized and non-standardized connector types may be developed and utilized in the future as new materials and fabrication techniques are introduced and as specific needs of practitioners change. For example, IS-4 type connectors are being introduced which combine two unipolar DF-1 type connectors and one bipolar IS-1 type connector in a single connector. IS-3 type connectors have also been considered, but have not become standardized.

It is often desirable to utilize more than one lead in conjunction with a single receptacle of an electrical therapeutic and/or diagnostic device. In order to do so, practitioners in the relevant art utilize connection adapters, which generally consist of a connector portion and a receptacle portion. These devices are generally designed to work with only a single connector type; that is, the receptacle portions of these devices are adapted to operatively accept only one type of connector. Utilizing the devices currently known in the art, practitioners are unable to utilize multiple leads having different connector types with a single receptacle of an electrical therapeutic and/or diagnostic device. It would be beneficial therefore, to provide an adapter configured in such a manner so as to enable practitioners to utilize stimulation leads with different types of connectors concurrently with a single receptacle of an electrical therapeutic and/or diagnostic device.

When utilizing two or more cardiac leads with an adapter, it is often desirable to delay the transmission of electrical signals to one or more of the leads connected to the adapter. For example, adapters of the present invention are used in some instances for bi-ventricular pacing or re-synchronization of the right and left ventricles in the treatment of congestive heart failure. In these applications, practitioners sometimes desire to introduce a predetermined delay in the delivery of the pacing energy (i.e., the electrical signal) from the electrical therapeutic device to the heart tissue via one or more cardiac leads.

It would therefore be beneficial to provide an adapter having circuitry for programmatically delaying the transmission of electrical signals from the electrical therapeutic and/or diagnostic device to one or more of the cardiac leads connected to the adapter, thereby permitting practitioners to control the sequence and timing of the transmission of signals to one or more cardiac leads.

SUMMARY OF THE INVENTION

The subject invention is directed to a new and useful lead adapter for use in conjunction with electrical stimulation leads such as, for example, cardiac and neurological stimulation leads designed to deliver electrical energy to tissue from an electrical stimulation device. A lead adapter constructed in accordance with an embodiment of the subject invention includes a connector portion having a connector configured for reception by an electrical stimulation device, and a receptacle portion electrically connected to the connector portion and having at least two receptacles for operatively accepting lead connectors. At least one of the receptacles is configured to operatively accept a different type of lead connector than another receptacle of the receptacle portion.

In one embodiment of the subject invention, the lead adapter includes a centrally located yoke portion, whereby the connector portion extends distally from the yoke portion and the receptacle portion extends proximally from the yoke portion. In another embodiment of the invention, the adapter includes a housing or block that defines the receptacle portion.

In one embodiment of the subject invention, the receptacle portion of the lead adapter is bifurcated in that it includes two receptacles. In a first instance, one receptacle is configured to accept a bipolar lead connector and the other receptacle is configured to accept a unipolar lead connector. In another instance, one receptacle is configured to accept a bipolar IS-1 type lead connector and the other receptacle is configured to accept a unipolar IS-1 type lead connector. In yet another instance, one receptacle is configured to accept an IS-1 type lead connector and the other receptacle is configured to accept an LV-1 type lead connector. In still another instance, one receptacle is configured to accept a bipolar IS-1 type lead connector and the other receptacle is configured to accept a unipolar LV-1 type lead connector. In another instance, one receptacle is configured to accept a bipolar IS-1 type lead connector and the other receptacle is configured to accept a bipolar LV-1 type lead connector. In yet another instance, one receptacle is configured to accept a unipolar DF-1 type lead connector and the other receptacle is configured to accept an bipolar IS-1 type lead connector. In certain instances the connector portion of the lead adapter includes a bipolar IS-1 type lead connector, and in other instances, the connector portion includes a bipolar LV-1 type lead connector. Other types of connectors may also be employed in the lead adapter.

In another embodiment of the subject invention, the receptacle portion is trifurcated in that it includes three receptacles. In one instance, one receptacle is configured to accept a bipolar lead connector and the other two receptacles are configured to accept unipolar lead connectors. In another instance, one receptacle is configured to accept a unipolar lead connector and the other two receptacles are configured to accept bipolar lead connectors. In yet another instance, one receptacle is configured to accept a bipolar IS-1 type lead connector and the other two receptacles are configured to accept unipolar DF-1 type lead connectors. In still another instance, one receptacle is configured to accept an LV-1 type lead connector and the other receptacles are configured to accept DF-1 type lead connectors. In certain instances the connector portion includes a tripolar in-line connector, and in other instances, the connector portion includes a quadru-polar in-line (IS-4 type) connector. Other types of connectors may also be employed in the lead adapter.

Any of the aforementioned embodiments of the lead adapter may also contain means for delaying the transmission of electrical signals from the electrical therapeutic and/or diagnostic device to one or more of the endocardial leads attached to the endocardial lead adapter, thereby allowing predetermined sequencing of electrical signal transmission to the various endocardial leads.

In a preferred embodiment of the subject invention, the lead adapter includes a yoke portion, a connector portion extending distally from the yoke portion and including a bipolar IS-1 type connector configured for reception within a corresponding port of an electrical stimulation device, and a bifurcated receptacle portion extending proximally from the yoke portion and electrically connected to the connector portion. The receptacle portion includes a first receptacle configured to operatively accept a unipolar LV-1 type lead connector and a second receptacle configured to operatively accept a bipolar IS-1 type lead connector.

In another preferred embodiment of the subject invention, the lead adapter includes a yoke portion, a connector portion extending distally from the yoke portion and including a bipolar IS-1 type connector configured for reception within a corresponding port of an electrical stimulation device, and a bifurcated receptacle portion extending proximally from the yoke portion and electrically connected to the connector portion. The receptacle portion includes a first receptacle configured to operatively accept a unipolar IS-1 type lead connector and a second receptacle configured to operatively accept a bipolar IS-1 type lead connector.

These and other aspects of the lead adapters of the subject invention will become more readily apparent to those having ordinary skill in the art from the following description of the invention taken in conjunction with th drawings described hereinbelow.

BRIEF DESCRIPTION OF THE DRAWINGS

So that those having ordinary skill in the art to which the subject invention pertains will more readily understand how to make and use the subject invention, preferred embodiments thereof will be described in detail hereinbelow with reference to the drawings, wherein.

DETAILED DESCRIPTION OF THE PREFERRED EMBODIMENTS

Figure 1:
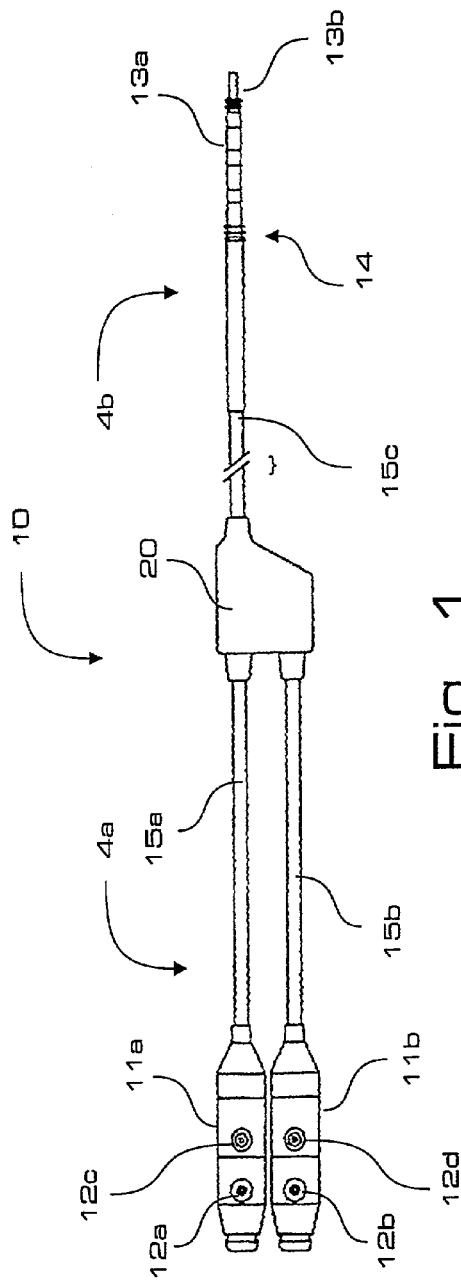
FIG. 1 is a plan view of a bifurcated lead adapter constructed in accordance with a preferred embodiment of the subject invention.

Referring now to the drawings wherein like reference numerals identify similar structural features of the several embodiments of the subject invention, there is illustrated in FIG. 1 a lead adapter constructed in accordance with a preferred embodiment of the subject invention and designated generally by reference numeral 10. Lead adapter 10 is a bifurcated adapter and includes a yoke portion 20 from which depends a proximal receptacle portion 4a and a distal connector portion 4b. The receptacle portion 4a includes two receptacles 11a and 11b for operatively receiving two different types of cardiac leads. For example, the leads can have different diameters, different lengths, different shapes or different electrical contact configurations.

In embodiments of the subject invention, the receptacles of the lead adapters can be configured to operatively accept, among other types of lead connectors, the following types of lead connectors: unipolar or bipolar IS-1 type lead connectors, unipolar or bipolar LV-1 type lead connectors, and unipolar DF-1 type lead connectors. Additionally, the connector portion of the lead adapter of the subject invention can include, among other types of connectors, a bipolar IS-1 type connector, a bipolar LV-1 type connector or a unipolar DF-1 type connector.

With continuing reference to FIG. 1, each receptacle of lead adapter 10 has a number of electrical poles which act as electrical connection points for electrically interfacing with associated cardiac leads. The receptacles are electrically connected to the connector 14 associated with the distal connector portion 4b by way of electrical conductors located in elongated flexible lumens 15a, 15b and 15c communicating with yoke portion 20. While lumens 15a and 15b are shown to have equal lengths, it is envisioned that lumens 15a and 15b can differ in length from one another (see FIG. 6). The electrical conductors contained in each lumen transmit electrical signals between cardiac leads operatively connected with heart tissue and an electrical therapeutic and/or diagnostic device.

Connector 14 of connector portion 4b has a bipolar configuration and includes two poles defined by connector ring 13a and connector pin 13b, respectively. Receptacle poles 12a and 12b and connector ring 13a are cathodic, while receptacle poles 12c and 12d and connector pin 13b are anodic. In particular, receptacle pole 12a of receptacle 1a is electrically connected in parallel with receptacle pole 12b of receptacle 11b, which are then electrically united to cathodic connector ring 13a of connector 14. Similarly, receptacle pole 12c of receptacle 11a is electrically connected in parallel with receptacle pole 12d of receptacle 11b, which are then electrically united with anodic connector pin 13b of connector 14.

In accordance with a preferred embodiment of the subject invention, receptacles 11a and 11b of lead adapter 10 have different pole dimensions in that receptacle 11a is configured to accept a bipolar lead with a first type of connector, such as a 1.8 mm connector, while receptacle 11b is configured to accept either a unipolar or bipolar lead with a second type of connector, such as an IS-1 (3.2 mm) connector. The connector portion 14 of lead adapter 10 is defined by a bipolar IS-1 (3.2 mm) connector.

Figure 6:
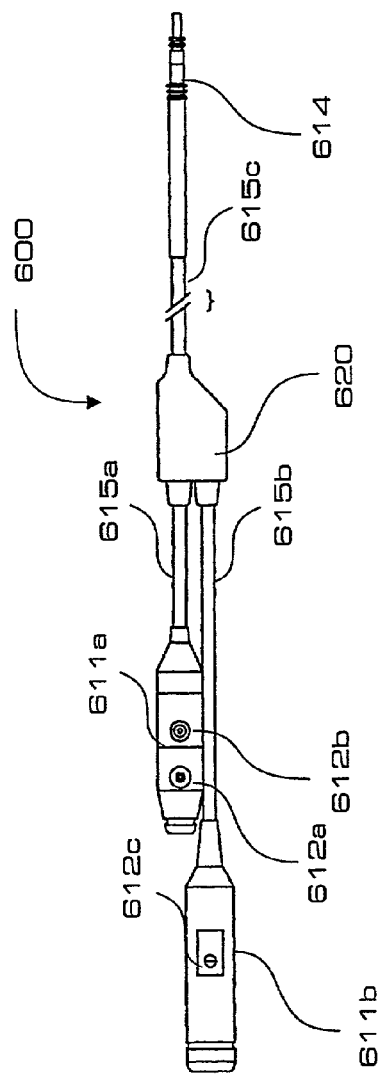
FIG. 6 is a plan view of another lead adapter constructed in accordance with a preferred embodiment of the subject invention.

It is envisioned that one of the receptacles of lead adapter 10 can be configured to accept a unipolar lead with an LV-1 (1.8 mm) type connector, as shown for example in FIG. 6. In this instance, the single pole of the unipolar LV-1 receptacle is electrically connected in parallel to the cathodic pole of the bipolar IS-1 (3.2 mm) receptacle, which are then electrically united with the cathodic pole of the connector. The anodic pole of the bipolar IS-1 receptacle is electrically connected to the anodic pole of the connector. It is also envisioned that the connector portion can be defined by a bipolar LV-1 type connector.

Figure 2:
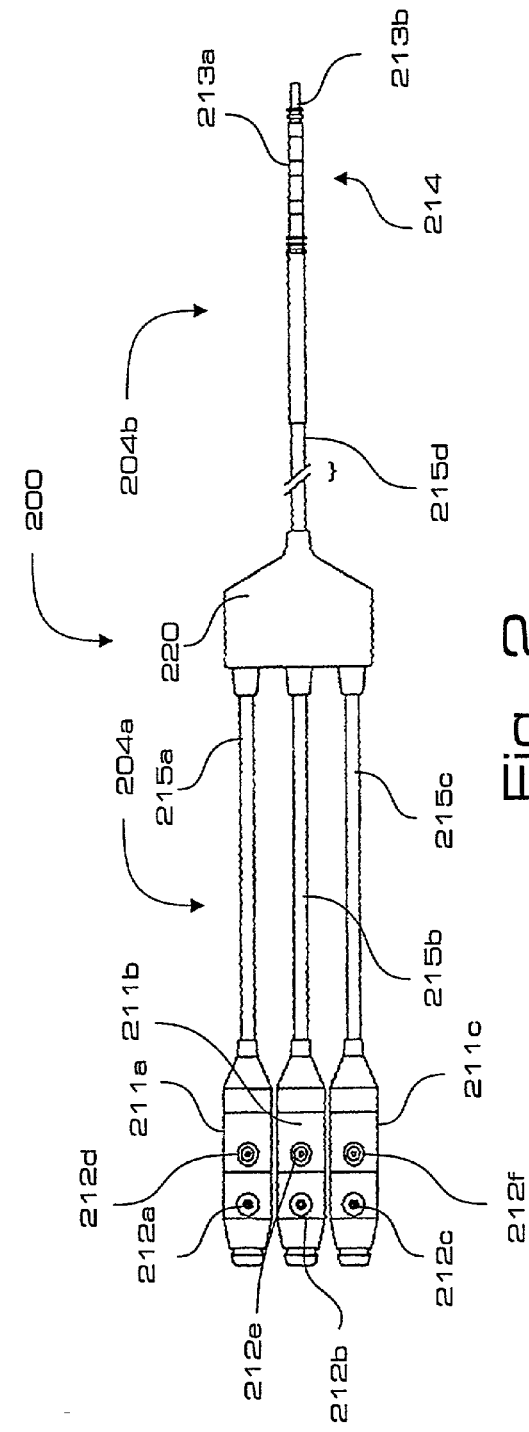
FIG. 2 is a plan view of a trifurcated lead adapter constructed in accordance with a preferred embodiment of the subject invention.

Referring now to FIG. 2, there is illustrated another lead adapter constructed in accordance with a preferred embodiment of the subject invention and designated generally by reference numeral 200. Lead adapter 200 is known as a trifurcated lead adapter and includes a yoke portion 220 from which extends a proximal receptacle portion 204a and a distal connector portion 204b. The receptacle portion 204a has three receptacles 211a, 211b and 211c each for operatively receiving a cardiac lead to establish electrical connectivity therewith.

Each receptacle is configured for unipolar or bipolar connectivity and includes two poles, 212a–212f, which act as electrical connection points for electrically interfacing with associated leads. The receptacles of receptacle portion 204a are electrically connected to the connector portion 204b by way of electrical conductors located in elongated flexible lumens 215a–215d which communicate with the yoke portion 220.

The connector portion 204b of lead adapter 200 includes a bipolar connector 214 having two poles defined by a cathodic connector ring 213a and an anodic connector pin 213b, for establishing and maintaining electrical contact with an electrical therapeutic and/or diagnostic device. Receptacle poles 212a, 212b and 212c are cathodic poles electrically connected in parallel and united at cathodic connector ring 213a of connector 214. Receptacle poles 212d, 212e and 212f are anodic poles electrically connected in parallel and united at the anodic connector pin 213b.

In accordance with a preferred embodiment of the subject invention, two of the three receptacles of lead adapter 200 may be configured to accept the same type of connector. For example, receptacles 211a and 211b are configured to accept the same type of connector while receptacle 211c is configured to accept a different type of connector. Similarly, receptacles 211a and 211c are configured to accept the same type of connector while receptacle 211b is configured to accept a different type of connector (see FIG. 5). Similarly, receptacles 211b and 211c are configured to accept the same type of connector while receptacle 211a is configured to accept a different type of connector. Alternatively, it is envisioned and well within the scope of the subject disclosure that the receptacles 211a, 211b and 211c are each configured to accept a different type of connector, either one of which may be unipolar or bipolar. In each instance, the connector 214 of connector portion 204b may be defined by a bipolar IS-1 (3.2 mm) type connector or an alternative bipolar connector.

Figure 3:
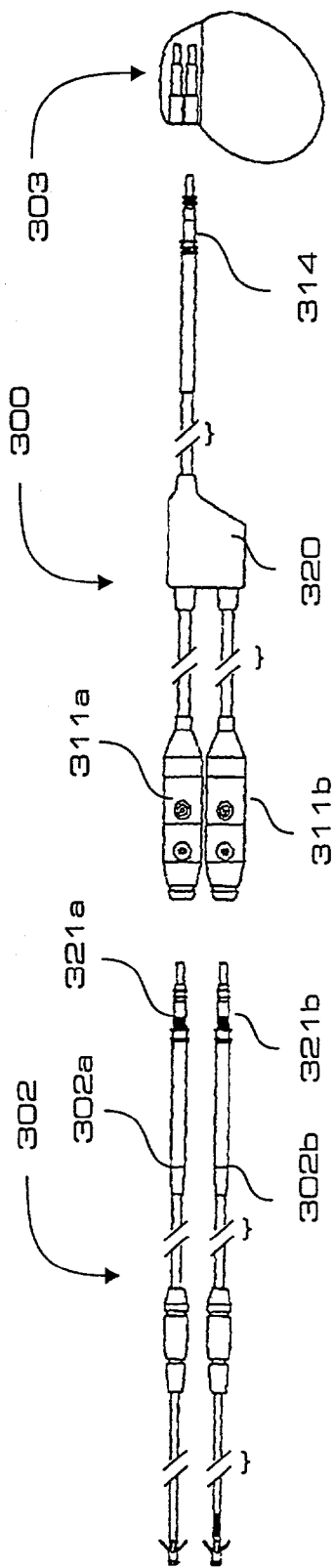
FIG. 3 is a plan view of two leads in position to be operatively connected to a bifurcated lead adapter of the subject invention, which in turn is in position to be operatively connected to an electrical stimulation device.

Referring now to FIG. 3, there is illustrated two passive fixation endocardial sensing/pacing leads 302a and 302b in position for operative connection with a bifurcated cardiac lead adapter constructed in accordance with a preferred embodiment of the subject invention and designated by reference numeral 300. Lead adapter 300 is in position for operative connection with a cardiac pacemaker 303. In this arrangement, lead 302a is a bipolar lead and has a 3.2 mm IS-1 type connector 321a positioned for operative connection with a bipolar 3.2 mm IS-1 type receptacle 311a of adapter 300. Upon connection, connector 321a will form an electrical connection with receptacle 311a, thereby permitting electrical signals to travel between receptacle 311a and connector 321a.

In contrast, lead 302b is a unipolar lead and has a larger 6 mm connector 321b positioned for operative connection with the 6 mm receptacle 311b of adapter 300. Upon connection, connector 321b will form an electrical connection with receptacle 311b, thereby permitting electrical signals to travel between receptacle 311b and connector 321b. As shown, bipolar IS-1 connector 314 extends distally from yoke portion 320 and is positioned to be operatively connected to cardiac pacemaker 303. Upon connection, bipolar IS-1 connector 314 will form an electrical connection with stimulation device 303, thereby permitting electrical signal to travel between device 303 and connector 314.

Figure 4:
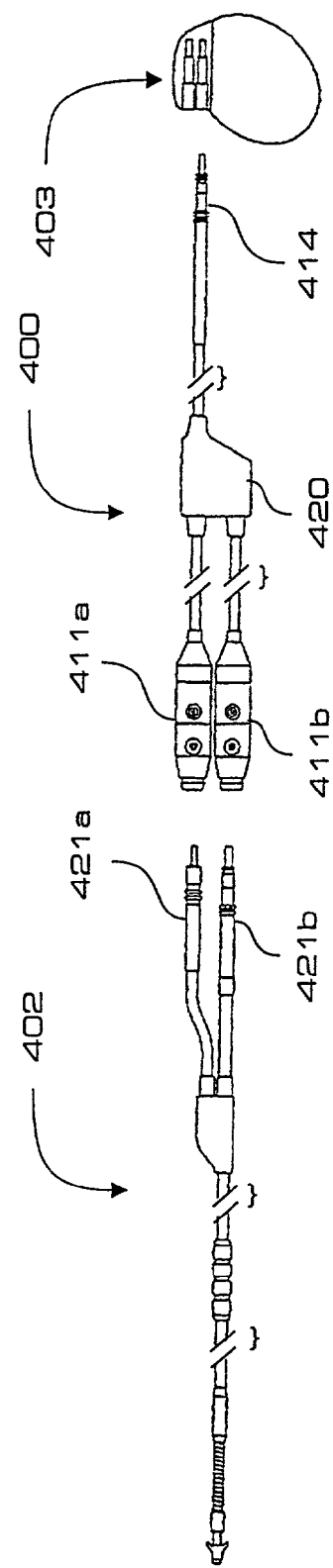
FIG. 4 is a plan view of a bifurcated lead with two connectors in position to be operatively connected to a bifurcated lead adapter of the subject invention, which in turn is in position to be operatively connected to an electrical stimulation device.

Referring now to FIG. 4, there is illustrated a bifurcated passive fixation endocardial pacing/sensing/defibrillation lead 402 in position for operative connection with a bifurcated lead adapter constructed in accordance with a preferred embodiment of the subject invention and designated generally by reference numeral 400. Lead adapter 400 is in position for operative connection with a cardiac pacemaker/implantable cardiac defibrillator 403. The endocardial lead 402 is bifurcated in that is has two connectors 421a and 421b. In this arrangement, connector 421a of lead 402 is a unipolar DF-1 type connector and is in position for operative connection with DF-1 type receptacle 411a of adapter 400. Upon connection, connector 421a will form an electrical connection with receptacle 411a thereby permitting electrical signal to travel between receptacle 411a, and connector 421a.

In contrast, connector 421b of lead 402 is a bipolar IS-1 type connector and is in position for operative connection with IS-1 type receptacle 411b of adapter 400. Upon connection, connector 421b will form an electrical connection with receptacle 411b, thereby permitting electrical signal to travel between receptacle 411b and connector 421b. Connector 414 of bifurcated lead adapter 400, which is preferably defined by a bipolar IS-1 type connector, extends distally from yoke portion 420 and is positioned to be operatively connected to cardiac pacemaker/implantable cardiac defibrillator 403. Upon connection, connector 414 forms an electrical connection with stimulation device 403, thereby permitting electrical signal to travel between device 403 and connector 411.

Figure 5:
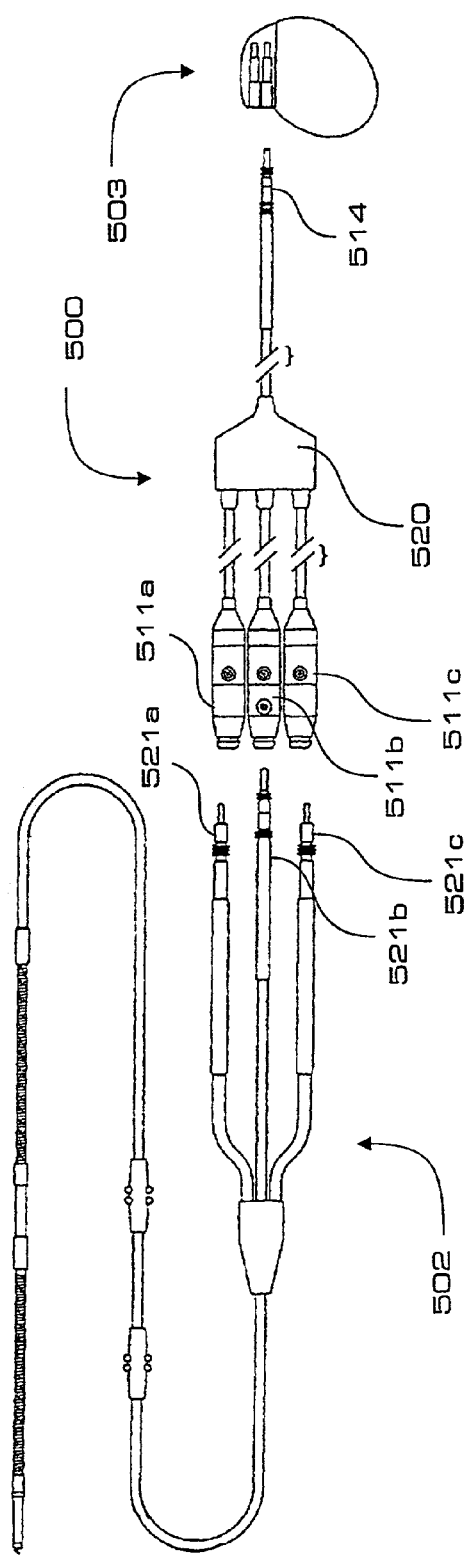
FIG. 5 is a plan view of an trifurcated lead with three connectors in position to be operatively connected to a trifurcated lead adapter of the subject invention, which in turn is in position to be operatively connected to an electrical stimulation device.

Referring to FIG. 5, there is illustrated an active fixation dual coil endocardial sensing/defibrillation lead 502 in position for operative connection with a trifurcated endocardial lead adapter constructed in accordance with a preferred embodiment of the subject invention and designated generally by reference numeral 500. Lead adapter 500 is in position for operative connection with an implantable cardiac defibrillator 503. Endocardial lead 502 is trifurcated in that it has three connectors 521a, 521b and 521c. By way of example, connector 521a is unipolar DF-1 type connector, connector 521b is a bipolar IS-1 type connector, and connector 521c is a second unipolar DF-1 type connector. Accordingly, trifurcated lead adapter 500 is configured such that receptacle 511a accepts a unipolar DF-1 type connector, receptacle 521b accepts a bipolar IS-1 type connector, and receptacle 511c accepts a unipolar DF-1 type connector. Those skilled in the art will readily appreciate that other combinations of connectors and receptacles can be arranged, and that receptacles 521a, 521b and 521c of adapter 500 can be configured to accept unipolar or bipolar connectors.

Connector 514 of trifurcated lead adapter 500, which is preferably defined by an in-line multipolar connector (e.g., a quadrupolar or IS-4 type connector), extends distally from the yoke portion 520 of adapter 500 and is in position to be operatively connected to cardiac defibrillator 503. Upon connection, multipolar in-line connector 514 forms an electrical connection with cardiac defibrillator 503, thereby permitting electrical signal to travel between cardiac defibrillator 503 and connector 514.

Referring to FIG. 6, there is illustrated another endocardial lead adapter constructed in accordance with a preferred embodiment of the subject invention and designated generally by reference numeral 600. Lead adapter 600 includes a yoke portion 620 from which extends two receptacles 611a and 611b. Receptacles 611a and 611b communicate with yoke portion 620 through corresponding flexible lumens 615a and 615b, respectively. Receptacle 611a is configured to operatively accept a bipolar IS-1 (3.2 mm) type lead connector, while receptacle 611b is configured to operatively accept a unipolar LV-1 (1.8 mm) type lead connector.

Receptacle 611a includes a cathodic pole 611a connected in parallel to the cathodic pole 612c of receptacle 611b and united at the cathodic pole of bipolar IS-1 type connector 614, while the anodic pole 612b of receptacle 611a is connected to the anodic pole of bipolar IS-1 type connector 614. Connector 614 communicates with yoke portion 620 by way of a flexible lumen 615c.

Figure 7:
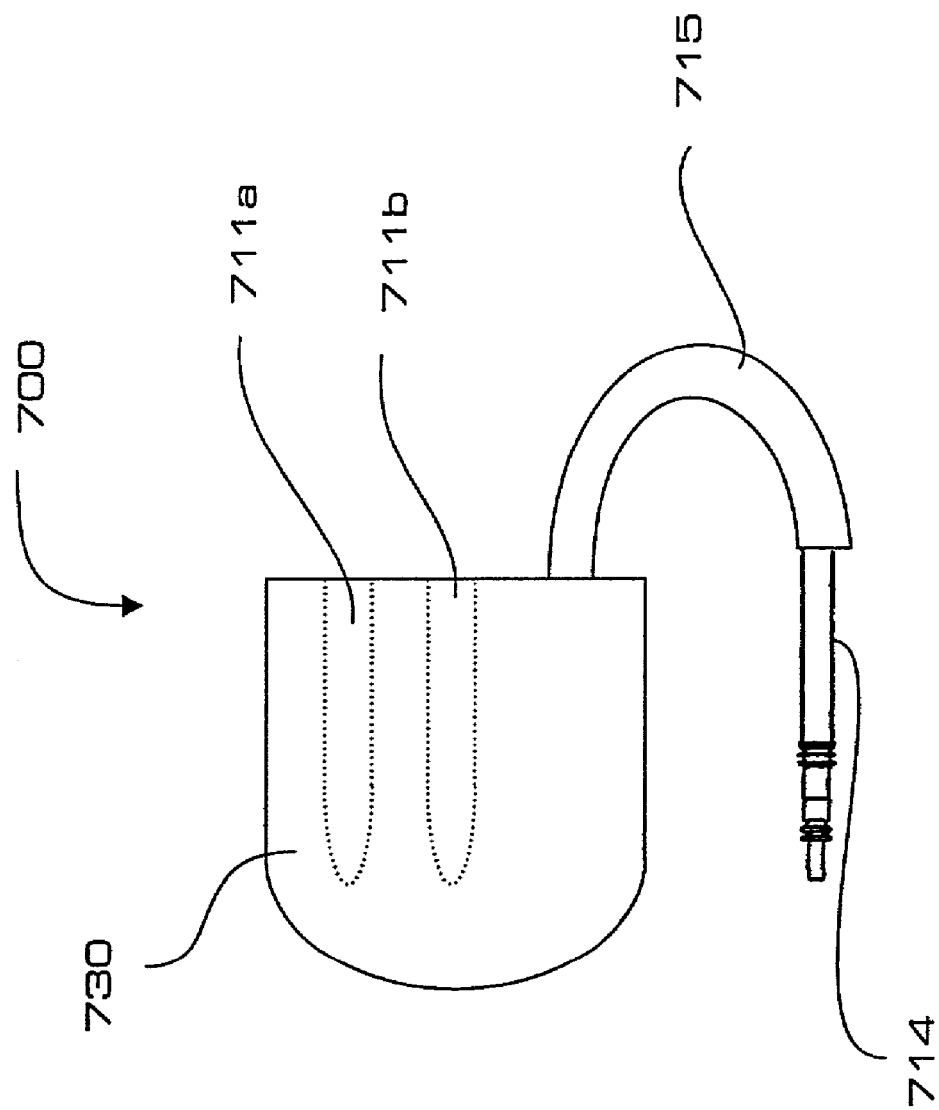
FIG. 7 is a plan view of a lead adapter block constructed in accordance with a preferred embodiment of the subject invention.

Referring now to FIG. 7, there is illustrated a lead adapter block constructed in accordance with a preferred embodiment of the subject invention and designated generally by reference numeral 700. Adapter block 700 includes a main housing 730 that defines a receptacle portion having two receptacles 711a and 711b configured to operatively accept lead connectors, and a connector 714 associated with the distal end of an elongated flexible lumen 715 extending from main housing 730.

Receptacles 711a and 711b of adapter block 700 are configured to accept two different types of lead connectors. For example, receptacle 711a can be configured to accept a unipolar LV-1 type receptacle, while receptacle 711b can be configured to accept a bipolar IS-1 type lead connector. Alternatively, receptacle 711a can be configured to accept a unipolar IS-1 type receptacle, while receptacle 711b can be configured to accept a bipolar IS-1 type lead connector. In another example, receptacle 711a can be configured to accept a bipolar LV-1 type receptacle, while receptacle 711b can be configured to accept a bipolar IS-1 type lead connector. In either instance, the connector 714 could be configured as a bipolar IS-1 type lead connector.

As noted hereinabove, when utilizing two or more endocardial leads with an adapter of the type disclosed herein, it is often desirable to delay the transmission of electrical signals to one or more of the leads connected to the adapter. For example, adapters of the present invention are used in some instances for bi-ventricular pacing or re-synchronization of the right and left ventricles in the treatment of congestive heart failure. In these applications, practitioners often desire to introduce a predetermined delay in the delivery of the pacing energy (i.e., the electrical signal) from the electrical therapeutic device to the heart tissue via one or more endocardial leads. This delay is typically less than 500 milliseconds, and may range from nearly 0 milliseconds to 500 milliseconds.

It is envisioned therefore, that lead adapters constructed in accordance with the subject invention include control circuitry disposed within the yoke portion for programmatically delaying the transmission of electrical signals from the electrical therapeutic and/or diagnostic device to one or more of the leads connected to the adapter. In doing so, practitioners can control the sequence and timing of the transmission of signals to one or more of the leads.

In each of the lead adapters disclosed herein, the lumens may be constructed of any suitable bio-compatible insulator material, such as, for example, silicone, and the electrical conductors extending through each lumen may be constructed of any suitable conductive material and may consist of one or more filaments.

Although the lead adapters of the subject invention has been described with respect to various embodiments and preferred embodiments, those skilled in the art will readily appreciate that changes and modifications may be made thereto without departing from the spirit and scope of the present invention as defined by the appended claims.

What is claimed is:

1. A lead adapter comprising:
   a) a connector portion including a bipolar IS-1 type lead connector configured for reception by an electrical stimulation device; and
   b) a receptacle portion electrically connected to the connector portion and having two receptacles for operatively accepting lead connectors, wherein one of the receptacles of the receptacle portion is configured to operatively accept a bipolar IS-1 type lead connector and the other receptacle of the receptacle portion is configured to operatively accept a unipolar LV-1 type lead connector.

2. A lead adapter as recited in claim 1, wherein the lead adapter includes a main housing, and wherein the connector portion extends distally from the main housing and the receptacle portion is formed integral with a proximal portion of the main housing.

3. A lead adapter as recited in claim 1, wherein the lead adapter includes a medial yoke portion, and wherein the connector portion extends distally from the yoke portion and the receptacle portion extends proximally from the yoke portion.

4. A lead adapter comprising:
   a) a yoke portion;
   b) a connector portion extending distally from the yoke portion and including a bipolar IS-1 type connector configured for reception within a corresponding port of an electrical stimulation device; and
   c) a bifurcated receptacle portion extending proximally from the yoke portion and electrically connected to the connector portion, the receptacle portion including a first receptacle configured to operatively accept a unipolar LV-1 type lead connector and a second receptacle configured to operatively accept a bipolar IS-1 type lead connector; wherein each receptacle is connected to the yoke portion by an elongated flexible lumen.

5. A lead adapter as recited in claim 4, wherein one elongated flexible lumen is longer than the other elongated flexible lumen.

6. A lead adapter as recited in claim 5, wherein the elongated flexible lumen associated with the first receptacle is longer than the elongated flexible lumen associated with the second receptacle.

7. A lead adapter comprising:
   a) a yoke portion;
   b) a connector portion extending distally from the yoke portion and including a bipolar type connector configured for reception within a corresponding port of an electrical stimulation device;
   c) a first receptacle portion configured to accept a unipolar type lead connector and connected to the yoke portion by a first elongated flexible lumen extending proximally from the yoke portion and having a first length; and
   d) a second receptacle portion configured to accept a bipolar type lead connector and connected to the yoke portion by a second elongated flexible lumen extending proximally from the yoke portion and having a second length; wherein the first receptacle portion is configured to accept a unipolar LV-1 type connector and the second receptacle portion is configured to accept a bipolar IS-1 type connector.

8. A lead adapter as recited in claim 7, wherein first receptacle portion is configured to operatively accept a unipolar type lead connector and the second receptacle portion is configured to operatively accept a bipolar type lead connector.

9. A lead adapter as recited in claim 8, wherein the length of the first elongated flexible lumen differs from the length of the second elongated flexible lumen.

10. A lead adapter as recited in claim 7, wherein the length of the first elongated flexible lumen is greater than the length of the second elongated flexible lumen.

* * * * *